US00PP12834P2

(12) United States Plant Patent
Slaughter et al.

(10) Patent No.: US PP12,834 P2
(45) Date of Patent: Aug. 6, 2002

(54) PEACH TREE NAMED 'BURPEACHEIGHT'

(75) Inventors: John K. Slaughter, Clovis; Timothy J. Gerdts, Kingsburg, both of CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 09/735,994

(22) Filed: Dec. 12, 2000

(51) Int. Cl.[7] ..... A01H 5/00

(52) U.S. Cl. ..... Plt./198

(58) Field of Search ..... Plt./198

*Primary Examiner*—Bruce R. Campell
*Assistant Examiner*—Susan B. McCormick
(74) *Attorney, Agent, or Firm*—Wells St. John P.S.

(57) ABSTRACT

A new and distinctive variety of peach tree denominated varietally as 'BURPEACHEIGHT' and which is characterized as to novelty by a date of maturity for commercial harvesting and shipment of, approximately August 30 to September 7, under the ecological conditions prevailing in the San Joaquin Valley of central California.

1 Drawing Sheet

BACKGROUND OF THE NEW VARIETY

The present invention relates to a new, novel and distinct variety of peach tree, *Prunus persica* which has been denominated varietally as 'BURPEACHEIGHT'. The 'BURPEACHEIGHT' Peach Tree produces an exceptionally high quality peach which is mature for harvesting and shipment in the late season. Still further, another unique aspect of the 'BURPEACHEIGHT' Peach Tree is that it yields a very firm peach which exhibits high eating quality as compared with the other peach varieties which ripen at approximately the same time of the season.

ORIGIN

The present variety of peach tree was derived from an ongoing program of fruit and nut tree breeding. The purpose of this program is to improve the commercial quality of deciduous fruit and nut varieties and rootstocks by creating and releasing selections of prunus, malus and regia species. To this end, we make both controlled and hybrid crosses each year in order to produce seedling populations from which improved progenies are evaluated and selected. The seedling 'BURPEACHEIGHT' was originated by us in 1994, and chosen from among a population of seedlings which resulted from a controlled cross of the 'Carnival' Peach Tree (U.S. Plant Pat. No. 2,144) which was used as the pollen parent, and the peach seedling A48-70, of unknown parentage, and which was used as the seed parent. The resulting seed from this cross was planted in the spring of 1995. The new variety was selected from among seedlings growing in the experimental orchards of The Burchell Nursery, INC. located near the city of Fowler, Calif., County of Fresno, in the Central San Joaquin Valley. The Peach Tree 'BURPEACHEIGHT' was subsequently marked and noted as having exceptional characteristics. It has been consecutively evaluated during the 1996–1999 fruiting seasons. After the 1996 season, 'BURPEACHEIGHT' was selected for advanced evaluation and repropagation.

ASEXUAL REPRODUCTION

Scionwood from the original seedling of the Peach Tree, 'BURPEACHEIGHT' was collected and grafted in the evaluation plot in the experimental orchard previously described and onto two different and existing 'Nemared' (unpatented) peach rootstocks in February of 1997. The resulting propagation (fruit and scion) have been subsequently evaluated for the 1997, 1998 and 1999 growing seasons. These evaluations clearly demonstrated that the repropagated trees are true to the fruiting and vegetative characteristics of the original seedling in all observable aspects.

DISTINCTIVE CHARACTERISTICS

The 'BURPEACHEIGHT' peach tree is characterized as to novelty by producing fruit which has a mid-season ripening date, and which is further of high quality, firm, and has an attractive exterior coloration. In this regard, the present variety of peach tree bears freestone fruit which are ripe for commercial harvesting on approximately August 30 to September 7. These harvesting dates are approximately one week earlier than the harvesting date of the commercial freestone peach variety 'Carnival' Peach Tree (U.S. Plant Pat. No. 2,144). The present variety distinguishes itself from the 'Carnival' Peach Tree by producing fruit having a brighter and more extensive exterior coloration, and has firmer flesh.

BRIEF DESCRIPTION OF THE DRAWING

The accompanying drawing is a color photograph. The photograph is of a characteristic twig bearing typical leaves; several leaves showing both the dorsal and ventral coloration; and further displaying several mature fruit showing their external coloration sufficiently matured for harvesting and shipment. Additionally, one fruit of the subject variety is dissected in the equatorial or cheek plane to illustrate the flesh and stone characteristics.

DETAILED DESCRIPTION

Referring more specifically to the pomological details of this new and distinct variety of peach tree, the following has been observed during the growing years 1999, and 2000 under the ecological conditions prevailing near the town of Fowler, county of Fresno, state of California. All major color code designations are by reference to The R.H.S. Colour Chart (Copyright 1995, Third Edition) provided by The Royal Horticultural Society of Great Britain.

Botanical classification: *Prunus persica* cultivar 'Burpeacheight'.

Tree:

*Size.*—Generally — Average to above average as compared to other common peach cultivars.

*Productivity.*—Productive.

*Figure.*—The original seedling was trained in a central leader configuration with a moderate spread in the crown of the tree. The tree is considered upright to upright spreading in form.

*Height.*—The original seedling had a height dimension of 3.99 m at the end of the 1999 growing season.

*Width.*—The original seedling tree had a width of 2.10 m at the end of the 1999 growing season.

*Current season growth.*—The current season growth for the new variety was approximately 0.73–0.88 m.

*Regularity of bearing.*—Regular, and considered hardy under typical central San Joaquin Valley conditions.

Trunk:

*Diameter.*—Approximately 13.7 cm in diameter when measured at a distance of approximately 15.24 cm above the soil level, at the end of the 2000 growing season.

*Bark texture.*—Considered moderately rough with numerous folds of papery scarf skin being present.

*Lenticels.*—Numerous flat, oval lenticels are present. The lenticels range in size from approximately 3.0 to 7.0 millimeters in width and from approximately 1 to 2 millimeters in height.

*Bark coloration.*—Variable, but it is generally considered to be a grey-brown (RHS Greyed-Orange Group 175 B).

Branches:

*Size.*—Considered medium for the variety.

*Diameter.*—The branches have a diameter of about 4.3 to 5.5 cm when measured during the $4^{th}$ year after grafting.

*Thickness.*—Average as compared to other varieties.

*Surface texture.*—Average, and appearing furrowed on wood which is several years old.

*Crotch angles.*—Variable between about 41° to 48° from the horizontal axis for scaffold limbs. This is not distinctive of the variety, however.

*Current season shoots.*—Surface texture — substantially glabrous.

*Internode length.*—Approximately 2.2 to 2.4 cm.

*Color of mature branches.*—Medium brown, RHS Greyed Orange Group (174 C to Greyed-Green Group 192 B).

*Current season shoots.*—Color — light green, RHS Yellow Green Group (144 C), with some reddish-brown coloration appearing on exposed exterior shoots, (RHS Greyed Red Group 181 B). The color of new shoot tips is considered a bright and shiny green, (RHS Green Group 143 B).

Leaves:

*Size.*—Considered average for the species. Leaf measurements have been taken from vigorous upright current season growth at mid-shoot.

*Leaf length.*—Approximately 170 to 174 millimeters.

*Leaf width.*—Approximately 47 to 53 millimeters.

*Leaf thickness.*—Approximately 1 to 2 millimeters.

*Leaf base shape.*—The leave base shape is slightly oblique.

*Leaf form.*—Lanceolate.

*Leaf texture.*—Glabrous.

*Leaf tip form.*—Acuminate.

*Leaf color.*—Dark green, (RHS Green Group 137 A).

*Lower surface.*—Light green, (RHS Yellow-Green Group 146 B).

*Venation.*—Finely pinnately veined.

*Mid-vein.*—Color — Light yellow green, (RHS Yellow Green Group 153 B).

*Leaf margins.*—Form — considered crenate, occasionally doubly crenate. Uniformity — considered generally uniform.

*Leaf petioles.*—Size — considered medium. Length — approximately 6 to 9 millimeters. Diameter — approximately 1.5 to 2 millimeters. Color — pale green, (RHS Yellow Green Group 144 C).

*Leaf glands.*—Size — Approximately one to two millimeters in height and two to three millimeters in width. Numbers — Generally 1–2 per side, occasionally two per side. Type — Reniform. Small. Color — Greenish brown, (RHS Grey Brown 199 C).

*Leaf stipules.*—Size — Medium for the variety. Length — Approximately 6 to 9 millimeters. Form — Lanceolate in form with a serrated margin. Color — Green, (RHS Yellow-Green 148A) when young but graduating to yellow-brown (RHS Greyed-Orange Group N167A) with advancing senescence. The stipules are considered to be early deciduous. Number — Typically 2 stipules per leaf bud and up to 6 per shoot tip are observed.

Flowers:

*Flower buds.*—Generally — The floral buds are considered to be small in size, plump to slightly pointed in form, and slightly appressed, relative to the bearing shoot.

*Flower buds.*—Color — The bud scales are gray-brown, (approximately RHS Greyed Orange Group 177 B). The buds are considered hardy under typical central San Joaquin Valley climatic conditions.

*Blooming type.*—Considered average in relation to other peach cultivars commonly growing in the central San Joaquin Valley. Date of full bloom was Mar. 8, 1998.

*Flower type.*—The variety is considered to be a showy type flower.

*Flower size.*—Flower diameter at full bloom is approximately 32 to 37 millimeters.

*Bloom quantity.*—Considered abundant.

*Flower bud frequency.*—Normally 1 to 2 buds appear per node, although 1 bud per node is more common.

*Petal size.*—Generally — Considered medium large for the species. Length — approximately 15 to 17 millimeters. Width — approximately 12 to 15 millimeters.

*Petal shape.*—Broadly ovate.

*Petal count.*—Nearly always 5.

*Petal texure.*—Glabrous.

*Petal color.*—Light pink when young, (approximately RHS Red Purple Group 68 B), and with advancing senescence to a very pale pink, (RHS Red Purple Group 68 D). The lower portion of the flower petal is RHS Red-Purple 167D.

*Petal claw.*—Form — The claw is considered truncate in shape and has small size when compared to other similar varieties. Length — approximately 1.5 to 2 millimeters. Width — approximately 1 millimeter.

*Petal margins.*—Generally — considered variable, from nearly smooth, to moderately undulate.

*Petal apex.*—Generally — The petal apices appear slightly domed.

*Flower pedicel.*—Length — considered medium-short, and having an average length of approximately 2.0 to 3.0 millimeters. Diameter — considered average, approximately 2 millimeters. Color — bright green, (RHS Yellow Green Group 144 D).

*Floral nectaries.*—Color — dull, orange, and occasionally orange-gold, (approximately RHS Greyed Orange Group 168 B). The Color of the nectaries become more dull and slightly darker with advancing senescence.

*Calyx.*—Surface Texture — generally glabrous, with slight ribbing. Color — a dull red, (approximately RHS Greyed Purple Group 184 A).

*Sepals.*—Surface texture — the surface has a medium length, wooly, and gray colored pubescence (RHS Greyed-Purple Group 183A). Size — average, and ovate in form. Color — a dull red, (approximately RHS Greyed Red Group 178 A). Number — Generally 5 per flower. Typically 5.0 millimeters wide and 6.0 millimeters in length.

*Anthers.*— Generally — average in size. Approximately 14.0 millimeters in width, and 1.0 millimeters in length. Color — red to reddish-orange dorsally, (approximately RHS Greyed Purple Group 187 D). Pollen production — pollen is abundant, and has a yellow-gold Color, (approximately RHS Orange 26 A).

*Filaments.*—Size — variable in length, approximately 14 to 16 millimeters. Color — RHS Red Purple Group 69 D.

*Pistil.*—Generally — average in size. Length — approximately 15 to 17 millimeters, including the Ovary. Color — considered a very pale green, at mid-bloom, (approximately RHS Yellow Green Group 151 D). Surface texture — the variety has a long, pale green to white pubescent pistil.

Fruit: Maturity when described: The present variety of fruit is described, as it would be found in its firm ripe condition at full commercial maturity. In this regard, the fruit of the present variety was first picked on approximately Aug. 30, 1998. The date of last pick of the same fruit in 1998 was approximately Sep. 7, 1998 under the ecological conditions prevailing in the San Joaquin Valley of central California.

*Size.*—Generally — medium in size, and considered moderately uniform.

*Average cheek diameter.*—approximately 76 to 78 millimeters.

*Average suture diameter.*—approximately 73 to 74 millimeters.

*Average axial diameter.*—approximately 74 to 76 millimeters.

*Fruit form.*—Generally — globose in its lateral aspect. The fruit is generally uniform in symmetry with a rounded and somewhat oblate form when viewed from the apical aspect.

*Fruit suture.*—Generally — the suture appears as a thin line and slightly depressed, and which extends from the base to the apex, and appears slightly deeper, basally, within the stem well, and apically on both sides of the pistil point. No apparent callousing or stitching exists along the suture line.

*Suture.*—Color — the suture normally is the same color as the underlying blush, both where the orange-yellow background, (RHS Orange Group N25 D) and the red orange color, (RHS Greyed Red Group 179 A to 179 B) occur.

*Ventral surface.*—Form — considered uniform.

*Stem cavity.*—Size — considered moderate for the species. Width — Approximately 19–21 millimeters. Length — Approximately 27–30 millimeters. Depth — Approximately 10 to 11 millimeters. Form — Considered narrowly oval.

*Fruit base.*—Generally — considered truncate in form, and uniform.

*Fruit apex.*—Generally — considered depressed and usually recessed below the height of the apical shoulders.

*Fruit stem.*—Generally — considered medium in length, approximately 9 to 10 millimeters. Diameter — approximately 3 to 4 millimeters. Color — generally a pale yellow-green, (approximately RHS Yellow Green Group 145 B).

*Fruit skin.*—Generally — considered medium or average in thickness. Surface texture — the variety has a short fine pubescent surface. Skin acidity — considered neutral.

*Tenacious to flesh.*—Yes at commercial maturity.

*Tendency to crack.*—Not observed.

*Skin color.*—Generally — variable, with approximately 70% to 80% of the fruit surface covered with a deep crimson red blush.

*Blush color.*—The blush color is generally more prevalent apically. This red blush color ranges from a dark red, (RHS Greyed Red Group 179 A and B, to RHS Red Group 45 B), with many degrees of shading and blending between these colorations.

*Skin ground color.*—This is generally present in variable percentages covering approximately 20% to 30% of the fruit's surface, and which is a Yellow-golden, (RHS Yellow Orange Group 22 A to 28 B).

*Flesh color.*—Generally — considered variable, from a yellow/orange, (RHS Yellow Orange Group 20 B to 22 C), occasionally areas of red radiate into the flesh from the pit area. This reddish color in the flesh ranges from (RHS Red Group 46 A to Yellow-Orange Group 22 B and 22C).

*Flesh fibers.*—Generally — Present, numerous, fine and lightly colored. These fibers are present throughout the flesh.

*Stone cavity.*—Color — Pink red, (from approximately RHS Red Group 52 A and Red Group 46 A, to a yellow orange, approximately RHS Yellow Orange Group 18 B).

*Flesh texture.*—Generally — the flesh is considered firm and fine at commercial maturity. Considered firm melting.

*Ripening.*—Generally — the fruit of the present variety ripens evenly.

*Flavor.*—Considered sweet and having moderate acidity. The flavor is considered both pleasant and balanced.

*Aroma.*—Pleasant, faint.

*Eating quality.*—Generally — considered good and well above average when compared to older common varieties.

Stone:

*Attachment.*—Generally — the stone is considered a freestone with a little air space at the cavity margin.

*Stone size.*—Generally — considered medium large for the species.

*Length.*—Approximately 32 to 35 millimeters.

*Width.*—Approximately 27 to 30 millimeters.

*Diameter.*—Approximately 21 to 23 millimeters.

*Fibers.*—Generally — a few medium length fibers are attached along the entire surface of the stone.

*Stone form.*—Generally — the stone is considered rounded to slightly oval.

*Stone base.*—The stone base is generally considered truncate.

*Base angle.*—The base angle of the stone is variable, but generally is considered oblique to the stone axis.

*Hilum.*—Generally — considered medium in size, and moderately defined. The hilum is approximately 5 to 7 millimeters long and approximately 3 to 4 millimeters wide. Form — considered oval.

*Apex.*—Shape — the stone apex is raised and has an acute tip.

*Stone shape.*—Considered variable. The stone is normally equal although occasionally may appear nearly unequal.

*Stone surface.*—Surface texture — generally considered medium in roughness and exhibits substantial pitting laterally. Substantial grooving is apparent over the apical shoulders. Surface pitting is prominent generally. Ridges — numerous fine ridges are present basally and converge towards the base of the stone.

*Ventral edge.*—Width — considered medium and prominent, and having a dimension of approximately 4 to 6 millimeters at mid-suture with the wings being most prominent over the basal area.

*Dorsal edge.*—Full, heavily grooved with jagged edges. Dorsal edge moderately eroded over the apical shoulder.

*Kernel.*—Kernel is mature when the fruit is ripe. Form — Oval. Length — approximately 20.0 millimeters. Width — approximately 16.0 millimeters. Thickness — approximately 5.0 millimeters. Pellicle — Considered pubescent. Color — RHS Greyed-Orange Group 166 C.

*Stone color.*—The color of the dry stone is approximately a light to medium brown, (RHS Orange Red Group 34 C).

*Tendency to split.*—No splitting noted.

*Use.*—The subject variety 'BURPEACHEIGHT' is considered to be a peach of mid-season maturity, having a very firm flesh, highly attractive color and which is useful for both local, long diatance, and export shipping.

*Keeping quality.*—Fruit has appeared to store well for as long as 18 days after harvest at temperatures of about 1.0° C.

*Resistance to insects and disease.*—No particular susceptibilities were noted.

*Shipping quality.*—Well above average.

Although this new variety of peach tree possesses the described characteristics noted above, as a result of the growing conditions prevailing in the central part of the San Joaquin Valley of Central California, it is to be understood that variations of the usual magnitude and characteristics incident to changes in growing conditions, fertilization, pruning and pest control are to be expected.

Having thus described and illustrated our new variety of peach tree what we claim as new and desire to secure by Plant Letters Patent is:

1. A new and distinct variety of peach tree substantially as illustrated and described and which is characterized as to novelty by producing an attractively colored freestone peach, which is sufficiently matured for harvesting and shipment approximately August 30 to September 7 under the prevailing ecological conditions experienced in the San Joaquin Valley of Central California.

* * * * *

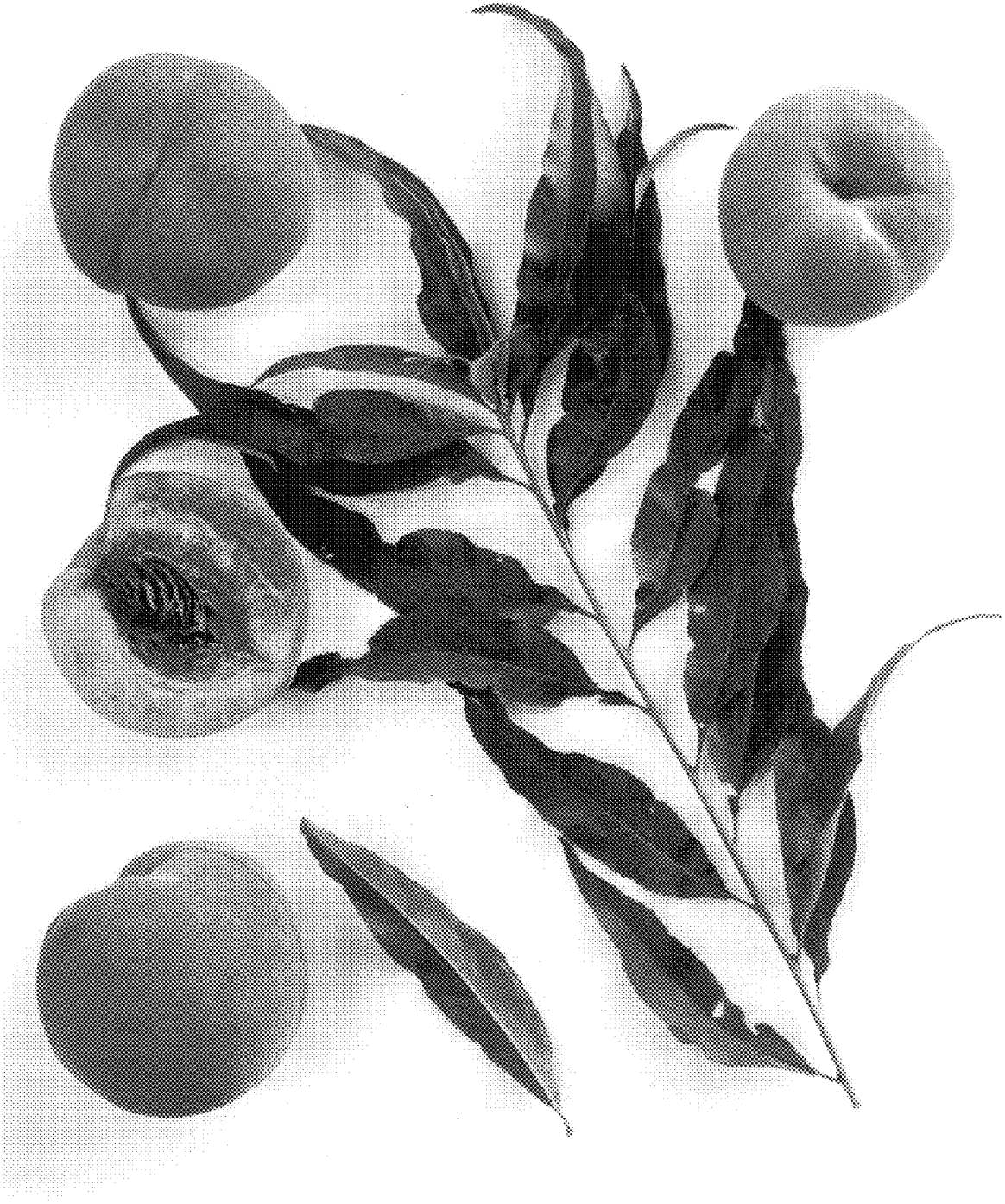

UNITED STATES PATENT AND TRADEMARK OFFICE

CERTIFICATE OF CORRECTION

PATENT NO. : PP 12,834 P2
DATED : August 6, 2002
INVENTOR(S) : John K. Slaughter et al.

It is certified that error appears in the above-identified patent and that said Letters Patent is hereby corrected as shown below:

Column 8,
Line 14, replace "long diatance," with -- long distance, --.

Signed and Sealed this

Eighth Day of April, 2003

JAMES E. ROGAN
*Director of the United States Patent and Trademark Office*